(12) United States Patent
Yanak et al.

(10) Patent No.: US 8,417,543 B2
(45) Date of Patent: *Apr. 9, 2013

(54) ELECTRONIC PAYMENT DELIVERY SERVICE

(75) Inventors: Edward Yanak, Denver, CO (US); Joseph Vause, San Mateo, CA (US); Joseph Kaberlein, Germantown, WI (US); Karen Cervenka, Foster City, CA (US)

(73) Assignee: Visa U.S.A. Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/818,023

(22) Filed: Jun. 17, 2010

(65) Prior Publication Data
US 2010/0332251 A1  Dec. 30, 2010

Related U.S. Application Data

(63) Continuation of application No. 11/829,041, filed on Jul. 26, 2007, now Pat. No. 7,769,599.

(60) Provisional application No. 60/834,584, filed on Jul. 31, 2006.

(51) Int. Cl.
G06Q 10/00 (2012.01)
G06Q 50/00 (2012.01)

(52) U.S. Cl.
USPC ............. 705/2; 705/3; 705/4; 705/30; 705/40

(58) Field of Classification Search .................. 705/2–4, 705/30, 40
See application file for complete search history.

(56) References Cited

U.S. PATENT DOCUMENTS

| 4,491,725 | A | 1/1985 | Pritchard |
| 5,018,067 | A | 5/1991 | Mohlenbrock et al. |
| 5,070,452 | A | 12/1991 | Doyle, Jr. et al. |
| 5,175,416 | A | 12/1992 | Mansvelt et al. |
| 5,235,507 | A | 8/1993 | Sackler et al. |

(Continued)

FOREIGN PATENT DOCUMENTS

| AU | 2006203957 | 3/2012 |
| AU | 2006203968 | 3/2012 |

(Continued)

OTHER PUBLICATIONS

Search/Examination Report dated Jul. 26, 2011 from Australian Patent Application No. 2007281260, 3 pages.

(Continued)

*Primary Examiner* — Michelle Le
(74) *Attorney, Agent, or Firm* — Cooley LLP; Walter G. Hanchuk; Nathan W. Poulsen

(57) ABSTRACT

Systems and methods for providing finance-related services such as electronic payment delivery are disclosed. In accordance with one embodiment, a payment system is configured to receive a payment message including a type of information, and to add an identification number to the message. The type of information is removed from the payment message, and the revised payment message is forwarded on to an entity responsible for payment. Particular embodiments in accordance with the present invention are suited for removing personal patient information from a HIPAA-compliant payment message, prior to forwarding the revised message over an electronic payment network.

22 Claims, 8 Drawing Sheets

U.S. PATENT DOCUMENTS

| | | | |
|---|---|---|---|
| 5,301,105 A | 4/1994 | Cummings, Jr. | |
| 5,324,077 A | 6/1994 | Kessler et al. | |
| 5,335,278 A | 8/1994 | Matchett et al. | |
| 5,550,734 A | 8/1996 | Tarter et al. | |
| 5,628,530 A | 5/1997 | Thornton | |
| 5,644,778 A | 7/1997 | Burks et al. | |
| 5,710,578 A | 1/1998 | Beauregard et al. | |
| 5,832,447 A | 11/1998 | Rieker et al. | |
| 5,915,241 A | 6/1999 | Giannini | |
| 5,965,860 A | 10/1999 | Oneda | |
| 5,995,939 A | 11/1999 | Berman et al. | |
| 6,012,035 A | 1/2000 | Freeman, Jr. et al. | |
| 6,044,352 A | 3/2000 | Deavers | |
| 6,082,776 A | 7/2000 | Feinberg | |
| 6,112,183 A | 8/2000 | Swanson et al. | |
| 6,151,588 A | 11/2000 | Tozzoli et al. | |
| 6,208,973 B1 * | 3/2001 | Boyer et al. | 705/2 |
| 6,332,133 B1 | 12/2001 | Takayama | |
| 6,343,271 B1 | 1/2002 | Peterson et al. | |
| 6,401,079 B1 | 6/2002 | Kahn et al. | |
| 6,529,884 B1 | 3/2003 | Jakobsson | |
| 6,629,081 B1 | 9/2003 | Cornelius et al. | |
| 6,850,901 B1 | 2/2005 | Hunter et al. | |
| 6,877,655 B1 | 4/2005 | Robertson et al. | |
| 6,915,265 B1 | 7/2005 | Johnson | |
| 6,988,075 B1 | 1/2006 | Hacker | |
| 7,072,842 B2 | 7/2006 | Provost et al. | |
| 7,174,302 B2 | 2/2007 | Patricelli et al. | |
| 7,295,988 B1 | 11/2007 | Reeves | |
| 7,428,494 B2 * | 9/2008 | Hasan et al. | 705/3 |
| 7,650,308 B2 | 1/2010 | Nguyen et al. | |
| 7,752,096 B2 | 7/2010 | Santalo et al. | |
| 7,769,599 B2 | 8/2010 | Yanak et al. | |
| 7,792,688 B2 | 9/2010 | Yanak et al. | |
| 7,866,548 B2 | 1/2011 | Reed et al. | |
| 7,925,518 B2 | 4/2011 | Lee et al. | |
| 7,996,260 B1 | 8/2011 | Cunningham et al. | |
| 2001/0037295 A1 | 11/2001 | Olsen | |
| 2001/0053986 A1 | 12/2001 | Dick | |
| 2002/0002534 A1 | 1/2002 | Davis et al. | |
| 2002/0002536 A1 | 1/2002 | Braco | |
| 2002/0019808 A1 | 2/2002 | Sharma | |
| 2002/0032583 A1 | 3/2002 | Joao | |
| 2002/0128863 A1 | 9/2002 | Richmond | |
| 2002/0138309 A1 | 9/2002 | Thomas, Jr. | |
| 2002/0147678 A1 | 10/2002 | Drunsic | |
| 2002/0152180 A1 | 10/2002 | Turgeon | |
| 2002/0198831 A1 | 12/2002 | Patricelli et al. | |
| 2003/0009355 A1 | 1/2003 | Gupta | |
| 2003/0040939 A1 | 2/2003 | Tritch et al. | |
| 2003/0055686 A1 | 3/2003 | Satoh et al. | |
| 2003/0193185 A1 | 10/2003 | Valley et al. | |
| 2003/0200118 A1 | 10/2003 | Lee et al. | |
| 2003/0212642 A1 | 11/2003 | Weller et al. | |
| 2003/0225693 A1 | 12/2003 | Ballard et al. | |
| 2004/0006490 A1 | 1/2004 | Gingrich et al. | |
| 2004/0039693 A1 | 2/2004 | Nauman et al. | |
| 2004/0054935 A1 | 3/2004 | Holvey et al. | |
| 2004/0103000 A1 | 5/2004 | Owurowa et al. | |
| 2004/0111345 A1 | 6/2004 | Chuang et al. | |
| 2004/0128201 A1 | 7/2004 | Ofir et al. | |
| 2004/0138999 A1 | 7/2004 | Friedman et al. | |
| 2004/0148203 A1 | 7/2004 | Whitaker et al. | |
| 2004/0172312 A1 | 9/2004 | Selwanes et al. | |
| 2004/0186746 A1 | 9/2004 | Angst et al. | |
| 2004/0210520 A1 | 10/2004 | Fitzgerald et al. | |
| 2004/0225567 A1 | 11/2004 | Mitchell et al. | |
| 2004/0254816 A1 | 12/2004 | Myers | |
| 2005/0010448 A1 * | 1/2005 | Mattera | 705/3 |
| 2005/0015280 A1 | 1/2005 | Gabel et al. | |
| 2005/0033609 A1 * | 2/2005 | Yang | 705/2 |
| 2005/0038675 A1 | 2/2005 | Siekman et al. | |
| 2005/0065819 A1 | 3/2005 | Schultz | |
| 2005/0065824 A1 | 3/2005 | Kohan | |
| 2005/0071194 A1 | 3/2005 | Bormann et al. | |
| 2005/0119918 A1 | 6/2005 | Berliner | |
| 2005/0182721 A1 | 8/2005 | Weintraub | |
| 2005/0187790 A1 | 8/2005 | Lapsker | |
| 2005/0187794 A1 | 8/2005 | Kimak | |
| 2005/0209893 A1 | 9/2005 | Nahra et al. | |
| 2005/0211764 A1 | 9/2005 | Barcelou | |
| 2005/0246292 A1 | 11/2005 | Sarcanin | |
| 2005/0273387 A1 | 12/2005 | Previdi | |
| 2005/0288964 A1 | 12/2005 | Lutzen et al. | |
| 2006/0010007 A1 | 1/2006 | Denman et al. | |
| 2006/0106645 A1 | 5/2006 | Bergelson et al. | |
| 2006/0106646 A1 | 5/2006 | Squilla et al. | |
| 2006/0111943 A1 | 5/2006 | Wu | |
| 2006/0129427 A1 | 6/2006 | Wennberg | |
| 2006/0129435 A1 | 6/2006 | Smitherman et al. | |
| 2006/0136270 A1 | 6/2006 | Morgan et al. | |
| 2006/0149529 A1 | 7/2006 | Nguyen et al. | |
| 2006/0149603 A1 | 7/2006 | Patterson et al. | |
| 2006/0149670 A1 | 7/2006 | Nguyen et al. | |
| 2006/0161456 A1 | 7/2006 | Baker et al. | |
| 2006/0173712 A1 | 8/2006 | Joubert | |
| 2006/0184455 A1 | 8/2006 | Meyer et al. | |
| 2006/0206361 A1 | 9/2006 | Logan, Jr. | |
| 2006/0224417 A1 | 10/2006 | Werner | |
| 2006/0229911 A1 | 10/2006 | Gropper et al. | |
| 2006/0235761 A1 | 10/2006 | Johnson | |
| 2007/0005403 A1 | 1/2007 | Kennedy et al. | |
| 2007/0027715 A1 | 2/2007 | Gropper et al. | |
| 2007/0061169 A1 | 3/2007 | Lorsch | |
| 2007/0106607 A1 | 5/2007 | Seib et al. | |
| 2007/0125844 A1 | 6/2007 | Libin et al. | |
| 2007/0143215 A1 | 6/2007 | Willems | |
| 2007/0282637 A1 | 12/2007 | Smith | |
| 2008/0010096 A1 | 1/2008 | Patterson et al. | |
| 2008/0071646 A1 | 3/2008 | Hodson et al. | |
| 2008/0140447 A1 | 6/2008 | Pourfallah et al. | |
| 2008/0147518 A1 | 6/2008 | Haider et al. | |
| 2008/0177574 A1 | 7/2008 | Gonzalez et al. | |
| 2008/0281733 A1 | 11/2008 | Kubo et al. | |
| 2008/0319794 A1 | 12/2008 | Carlson et al. | |
| 2008/0319904 A1 | 12/2008 | Carlson et al. | |
| 2009/0006203 A1 | 1/2009 | Fordyce, III et al. | |
| 2010/0100484 A1 | 4/2010 | Nguyen et al. | |
| 2010/0332251 A1 | 12/2010 | Yanak et al. | |
| 2011/0178816 A1 | 7/2011 | Lee et al. | |

FOREIGN PATENT DOCUMENTS

| | | |
|---|---|---|
| EP | 1834275 | 9/2007 |
| EP | 1834314 | 9/2007 |
| EP | 1856663 | 11/2007 |
| EP | 2030163 | 3/2009 |
| EP | 2035990 | 3/2009 |
| EP | 2165297 | 3/2010 |
| HK | 1107164 | 3/2008 |
| HK | 1107172 | 3/2008 |
| HK | 1108752 | 5/2008 |
| JP | 2005124991 | 5/2005 |
| JP | 2008545210 | 12/2008 |
| JP | 2009541864 | 11/2009 |
| KR | 1020040028017 | 4/2004 |
| KR | 1020050099707 | 10/2005 |
| KR | 1020050094938 | 7/2006 |
| KR | 1020070041183 | 4/2007 |
| WO | WO99/22330 | 5/1999 |
| WO | WO01/06468 | 1/2001 |
| WO | WO03/073353 | 9/2003 |
| WO | WO2006/074285 | 7/2006 |
| ZA | 201000032 | 4/2011 |

OTHER PUBLICATIONS

"Welcome to American Express Healthpay Plus(SM)", What is HealthPay Plus downloaded on www.152.americanexpress.com/entcampWeb/WhatIsHealthPayPlus.jsp at Feb. 2, 2007 p. 1-3.

"Welcome to American Express Healthpay Plus Works, What is Healthy Pay Plus" downloaded on www.152.americanexpress.com/entcampWeb/payment.sub.--technologies/epay.su- b.--how.sub.--it.sub.--works.jsp at Feb. 2, 2007, p. 1-2.

"Welcome to American Express Healthpay Plus Works", How to Reconcile Payments downloaded on www.152.americanexpress.com/entcampWeb/HowToReconcilePayments.jsp at Feb. 2, 2007, p. 1-2.

"Visa USA Small Business & Merchants, Visa ePay—How it Works" downloaded on www.usa.visa.com/business/accepting.sub.--visa/payment.sub.--technolog- ies/epay.sub.--how.sub.--it.sub.--works.html at Feb. 2, 2007; p. 1.

"Visa USA Small Business & Merchants, Visa ePay—Participating Financial Institutions" downloaded on www.usa.visa.com/business/accepting.sub.--visa/payment.sub.--technologies- /ePay.sub.--fi.html at Feb. 2, 2007; p. 1.

"Visa USA Small Business & Merchants, Visa ePay—Credit Counseling Automation" downloaded on www.usa.visa.com/business/accepting.sub.--visa/payment.sub.--technologies- /epay.sub.--credit.sub.-counseling.html at Feb. 2, 2007; p. 1-3.

"Visa Introduces Next Generation B2B Payment Service" downloaded on www.sellitontheweb.com/ezine/news0569.shtml at Feb. 2, 2007; p. 1-4.

"Visa Introduces Next Generation B2B Payment Service" downloaded on www.corporate.visa.com/md/nr/press136.jsp at Feb. 2, 2007 ; p. 1-3.

"Visa ePay" downloaded on www.usa.visa.com/business/accepting.sub.--visa/payment.sub.--technologies- /epay.html at Feb. 2, 2007; p. 1.

Companion Guide 835 Health Care Claim Payment/Advice, Convansys, Jun. 24, 2004 XP002564865 http://www.njelkids.com/UL/pdf/NJ_835v1_20040820-2.pdf.

Hammond, W Edward and Cimino, James "Standards in Medical Informatics: Computer Applications in Health Care and Biomedicine," 2000 Springer, NY XP002564866, pp. 226-276.

Classen, David et al.; "The Patient safety Insitute demonstration Project: A Model for Implementing a Local Health information Infrastructure"; 2004, Journal of Healthcare Information Management, vol. 19, No. 4, pp. 75-86.

"Patient Safety Institute: Economic Value of a Community Clinical Information Sharing Network, Part 1: Value to Payers (Private, Medicare, Medicaid and self-Insured Employers) and the Uninsured"; White Paper prepared by Emerging Practives First consulting Group, 2004. pp. 1-18.

"Visa Introduces Next Generation B2B Payment Service" downloaded on www.corporate.visa.com/md/nr/press136jsp, Feb. 2, 2007, pp. 1-3.

"Visa USA Small Business & Merchants, Visa ePay—How it Works" downloaded on www.usa.visa.com/business/accepting_visa/payment_technologies/epay_how_it_works.html, Feb. 2, 2007, p. 1.

"Visa USA Small Business & Merchants, Visa epay—Participating Financial Institutes" downloaded on www.usa.visa.com/business/accepting_visa/payment_technologies/epay_fi.html , at Feb. 2, 2007, p. 1.

"Visa ePay" downloaded on www.usa.visa.com/business/accepting_visa/payment_technologies/epay.html, Feb. 2, 2007, p. 1.

"Welcome to American Express Healthpay Plus Works, What is Pay Plus" downloaded on www.152.americanexpress.com/entcampweb/payment_technologies/epay_how_it_works.jsp, Feb. 2, 2007, pp. 1-2.

"Visa USA Small Business & merchants, Visa ePay—Credit counseling Automation" downloaded on www.usa.visa.com/business/accepting_visa/payment_technologies/epay_credit_counseling.html, Feb. 2, 2007, pp. 1-3.

"Visa Introduces Next Generation B2Bpayment Service" downloaded on www.sellitontheweb.com/ezine/news0569.shtml, Feb. 2, 2007, pp. 1-4.

"Welcome to American Express Healthpay Plus(SM)", What is HealthPay Plus downloaded on www.152.americanexpress.com/entcampweb/whatishealthpayplus.jsp at Feb. 2, 2007, pp. 1-5.

Supplementary European Search Report for EP 06717481.
International Search Report for PCT/US2006/00288.
Supplementary European Search Report for EP 06717470.
International Search Report for PCT/US2006/00274.
Supplementary European Search Report for EP 06717482.
International Search Report for PCT/US2007/70780.
Supplementary European Search Report for European Patent Application EP 07798894.
International Search Report for PCT/US2007/71797.
Supplementary European Search Report for EP 08771445.7.
Recal Introduces WebSentry Reducing the Risk of Fraud for Internet Transactions; WebSentry Offers System Integrators Cost Effective SET Compliance for E-Commerce—Canadian Corporation News May 26, 1999.

* cited by examiner

ELECTRONIC PAYMENT DELIVERY SERVICE

CROSS-REFERENCE TO RELATED APPLICATION

This application is a continuation application of U.S. patent application Ser. No. 11/829,041, filed on Jul. 26, 2007, which is a non-provisional of and claims the benefit of U.S. Provisional Patent Application No. 60/834,584, filed on Jul. 31, 2006, which are all herein incorporated by reference in their entirety for all purposes.

BACKGROUND

Data communications networks are widespread in the United States. Many types of messages and transactions are sent through such networks, including electronic mail, news stories, and financial transactions.

Some data networks provide mechanisms for transmitting payment information from a merchant to a financial institution and vice versa. These networks are sometimes referred to as payment processing networks.

Payment processing networks are generally highly reliable, secure, and fast. Point of sale (POS) terminals coupled to such payment processing networks are generally widely available at merchants and other locations.

While ubiquitous in mainstream commerce, payment processing networks have so far not enjoyed widespread use in certain specialized fields, for example the healthcare industry. Specifically, it is estimated that every year there occur eight billion healthcare payment transactions representing roughly US $1.4 trillion.

FIG. 1 is a schematic diagram illustrating a simplified view of conventional payment processing in the healthcare field. Specifically, FIG. 1 shows the conventional series of payment processing interactions 100 occurring between a healthcare payer 101, healthcare provider 102, and a financial institution 104 of the healthcare provider. Examples of healthcare payers 100 include insurance companies. Examples of healthcare providers 102 include hospitals, doctor's offices, and pharmacies. Examples of financial institutions 104 include banks. For purposes of this patent application, the terms "payer" and "payor" are used interchangeably.

FIG. 1 shows the series of steps involved in conventional healthcare payment processing. Once a patient has visited healthcare provider 102, in a first step 110 the provider submits, typically by form mailed to payer 101, a healthcare claim in compliance with §837 of the Health Insurance Portability and Accountability Act (HIPAA). Enacted in 1996, HIPAA sets forth requirements addressing the security and privacy of health data.

Payer 101 receives the healthcare claim, and reviews it for eligibility to for payment under existing agreements with the patient and with the healthcare provider. Based upon the results of this review, in step 112 payer 101 returns to the healthcare provider 102 an Explanation of Benefits (EOB), indicating the amount to be paid (if any) by payer 101 for the medical services or products rendered to the patient by the healthcare provider.

Payer 101 also provides payment to the healthcare provider based upon the EOB. As shown in step 114, for approximately 75% of all claims, payment from the payer to the healthcare provider takes the form of a paper check. In step 116, this paper check must be forwarded on to the healthcare provider's financial institution 104.

In a minority of cases, payment from payer 101 to healthcare provider 102 may take the form of an Automated Clearing House (ACH) transfer 118 of funds to financial institution 104 of the healthcare provider 102. Whether payment is provided to the healthcare provider by paper check or by ACH transfer, in step 120 the financial institution 104 must report to healthcare provider 102, the status of the transactions through a bank statement.

The conventional healthcare payment processing flow shown and described in connection with FIG. 1 is characterized by a high intensity of manual labor. Specifically, conducting financial transactions by paper check (the vast majority of the payment transactions) requires proper handling and routing of paper checks at every stage of the process. Moreover, the healthcare provider is required to manually reconcile the payment amount with the data provided in the EOB and the original Healthcare Claim submitted under HIPAA. Such labor intensive activities drive up the cost of the payment process and of the process for patients to inquire about the status of their healthcare claims, and dispute those claims if appropriate.

In addition, HIPAA mandated changes within the healthcare industry, including the adoption of standardized electronic data interchange (ED) message formats to exchange information, and the utilization of electronic forms of payment. Accordingly, banks, healthcare companies, and third party processing providers have an incentive to bring the healthcare market the degrees of reliability, interoperability, security, and automation that exists in banking and the traditional payments arena.

Therefore, it would be desirable to provide a method and system facilitating the use of payment processing networks in the context of the healthcare industry.

SUMMARY

Embodiments in accordance with the present invention relate to systems and methods for providing finance-related services such as electronic payment delivery are disclosed. In accordance with one embodiment, a payment system is configured to receive a payment message including a type of information, and to add an identification number to the message. The type of information is removed from the payment message, and the revised payment message is forwarded on to an entity responsible for payment. Particular embodiments in accordance with the present invention are suited for removing personal patient information from a HIPAA-compliant payment message, prior to forwarding the revised message over an electronic payment network.

Embodiments of the invention are directed to systems and methods for routing funds, remittance data, and other financial information. The information can be routed between parties, such as from institutions offering services such as bill payment or credit counseling to financial institutions performing services such as collection and payment processing on behalf of billers. The information can be any appropriate information, such as transaction-based information or non-financial management information. Data can flow between end users, such as from a consumer to a biller, through the electronic payment delivery system, and can also pass through other entities such as a payment originator and a biller financial institution. The payment service can provide functionality such as payment, settlement, and financial reporting. The data can be transferred and stored in any appropriate format useful for financial institutions and the like. Particular embodiments in accordance with the present invention are particularly suited for use in the healthcare industry for processing payment requests in compliance with §835 of HIPAA.

An embodiment of a system in accordance with the present invention comprises a host computer comprising a processor and a computer readable storage medium. The computer readable storage medium has code stored thereon to direct the processor to receive a first payment message from a first entity, recognize a type of information in the first payment message, and generate a revised payment message with an identifier, and without the type of information. Code stored on the computer readable storage medium also directs the processor to forward the revised payment message to a second entity to execute or facilitate the execution of a payment.

An embodiment of a method in accordance with the present invention for processing a healthcare payment, comprises, receiving from a healthcare payer, a first electronic message instructing payment of a healthcare claim. A type of information is recognized in the first electronic message. A revised payment message is generated with an identifier and without the type of information. The revised payment message is forwarded to a second entity to generate or facilitate execution of a payment.

An alternative embodiment of a method in accordance with the present invention, comprises, sending to a processor, a first electronic message instructing payment of a healthcare claim. A computational apparatus at the processor recognizes in the first electronic message a type of information, generates a revised payment message with an identifier and without the type of information, and then forwards the revised payment message to a second entity to generate or facilitate execution of a payment. Notification of the payment is then received.

An alternative embodiment of a system in accordance with the present invention comprises, a processor configured to receive a first electronic message instructing payment of a healthcare claim; and a computational apparatus at the processor. The computational apparatus is configured to recognize in the first electronic message a type of information, and generate a revised payment message with an identifier and without the type of information. The computational apparatus is further configured to forward the revised payment message to a second entity to generate or facilitate execution of a payment; and to receive notification of the payment.

Other embodiments of the invention are directed to systems and methods using, accessing, and/or providing the above-described functionality and services.

These and other embodiments of the invention are described in further detail below.

DETAILED DESCRIPTION

Figure 1:
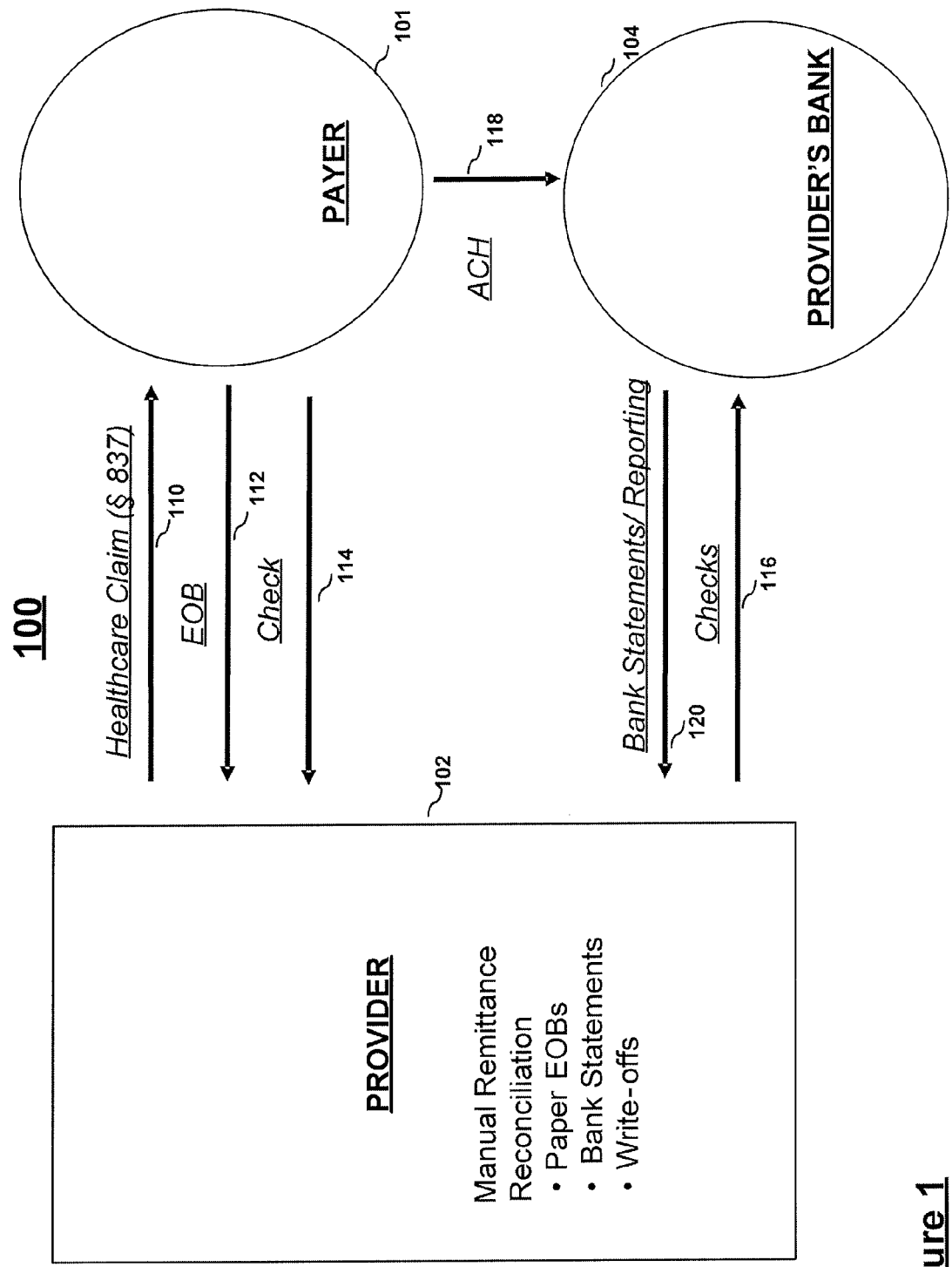
FIG. 1 shows a simplified schematic view of a conventional process flow for payment of healthcare claims.

Embodiments in accordance with the present invention relate to systems and methods for providing finance-related services such as electronic payment delivery are disclosed. In accordance with one embodiment, a payment system is configured to receive a first payment message including a type of information, and to add an identifier such as an identification number to form a revised payment message. The first payment message may or may not be the initial electronic message that is sent in response to an interaction between a patient and a healthcare provider, and may have been sent by a first entity such as a payer. In embodiments of the invention, the type of information is removed from the first payment message, and the revised payment message is forwarded on to a second entity that is responsible for payment or that can help facilitate payment. Particular embodiments in accordance with the present invention are suited for removing personal patient information from a §835 HIPAA-compliant payment message, prior to forwarding the revised message over an electronic payment network.

Embodiments of the invention are directed to systems and methods for routing funds, remittance data, and other financial information. The information can be routed between parties, such as from institutions offering services such as bill payment or credit counseling to financial institutions performing services such as collection and payment processing on behalf of billers. The information can be any appropriate information, such as transaction-based information or non-financial management information. Data can flow between end users, such as from a consumer to a biller, through the electronic payment delivery system, and can also pass through other entities such as a payment originator and a biller financial institution. The payment service can provide functionality such as payment, settlement, and financial reporting. The data can be transferred and stored in any appropriate format useful for financial institutions and the like.

In accordance with one embodiment of the present invention, the payment system may be used in conjunction with the confidential payment of healthcare claims in compliance with HIPAA. In certain such embodiments, an entity in the system is responsible for receiving from a payer a payment message in compliance with §835 of HIPAA, stripping certain personal information from the payment message, and inserting an identification number into the message prior to forwarding the modified message onto an entity responsible for debiting funds from a financial institution of the payer, and crediting those funds to the financial institution of the healthcare provider. In accordance with certain embodiments, a third party healthcare processor may receive the message from the payer and be responsible for stripping the personal information and inserting the identification number. In accordance with other embodiments, an administrator of the payment processing system itself may be receive an unaltered message directly from the payer, and be responsible for the stripping and ID insertion functions.

The payment delivery service can be provided using any appropriate hardware, software, and network known or used in the art for such purposes. In one example, a central server or server cluster receives an electronic message from a client computer over a network such as the Internet, processes information in the message, extracts any applicable related information from a central database, and sends a subsequent message or batch or messages to a computer or processor for a financial institution. Various computer and processing networks are known and used in the art that can be similarly used for such purposes as known in the art.

In accordance with certain embodiments of the present invention, invention, a Universal Biller File (UBF) can be utilized to contain key payment data for participating billers. This allows biller financial institutions to receive properly structured data, as well as the easy generation of financial reports and exporting of financial data.

Figure 2:
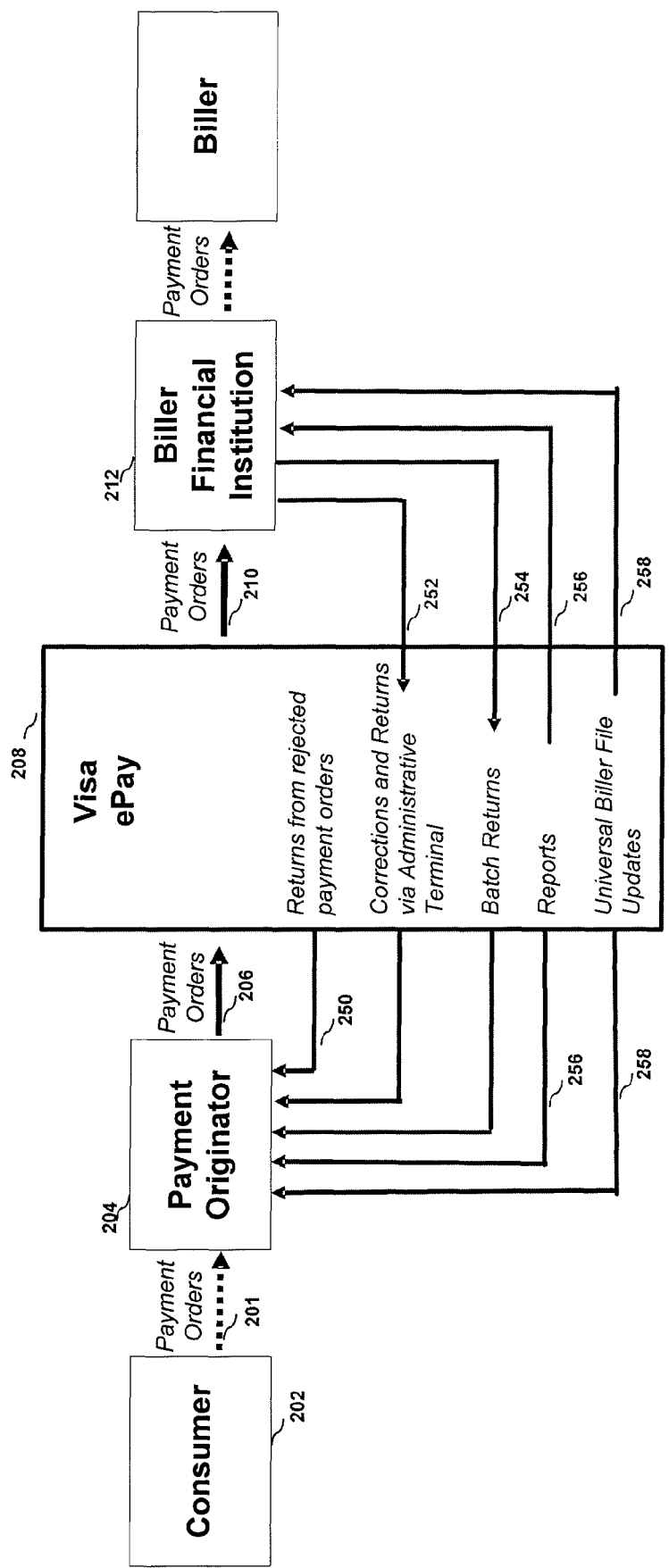
FIG. 2 shows a simplified schematic view of interactions of an embodiment of a payment system in accordance with the teachings of the present invention.

FIG. 2 shows a simplified schematic diagram showing interaction 200 between an embodiment of an electronic payment system in accordance with the present invention, and other entities. As shown in FIG. 2, in step 201 consumer 202 interacts with payment originator 204, for example by making a purchase from a merchant. In step 206, the payment originator 204 interacts with electronic payment system 208 in accordance with an embodiment of the present invention.

In step 208, electronic payment system 208 in turn forwards the payment order to the biller financial institution 212, which in step 214 forwards the payment order to biller 216.

As shown in FIG. 2, electronic payment system 208 may perform a variety of functions to expedite efficient handling of payment processing operations. For example, as shown in step 250 the payments system 208 may return rejected payment orders to the payment originator.

In addition, the electronic payment system 208 may serve as an effective intermediary between biller financial institution 212 and payment originator 204. For example, as shown in sep 252, the biller financial institution 212 may forward to payment originator 204 corrections and returns via an administrative terminal controlled by the payment system 208. Alternatively or in addition, as shown in step 254 the biller financial institution 212 may forward batch returns to the payment originator 204 via payment system 208.

As shown in FIG. 2, payment system 208 may itself be responsible for generating particular information for forwarding to both the biller financial institution 212 and the payment originator 204. In particular, in step 256, the electronic payment system may create and distribute reports of payment transactions to biller financial institution 212 and payment originator 204.

In addition, as shown in step 258, the electronic payment system 208 may distribute to payment originator 204 and biller financial institution 212, updates to the Universal Biller File (UBF). In accordance with specific embodiments, the electronic payment system may include a UBF which provides one or more of the following functionalities.

The UBF may function as a central database containing key payment data for participating Billers. Examples of key biller data stored by the UBF may include but are not limited to biller ID, name and address, financial institution ID and account number, and accounts receivable account structure, masks, and edit rules. Utilizing the UBF, biller financial institutions receive properly structured data after editing process. The UBF may also provide an online report viewer, and weekly distribution of relevant information.

Figure 2A:
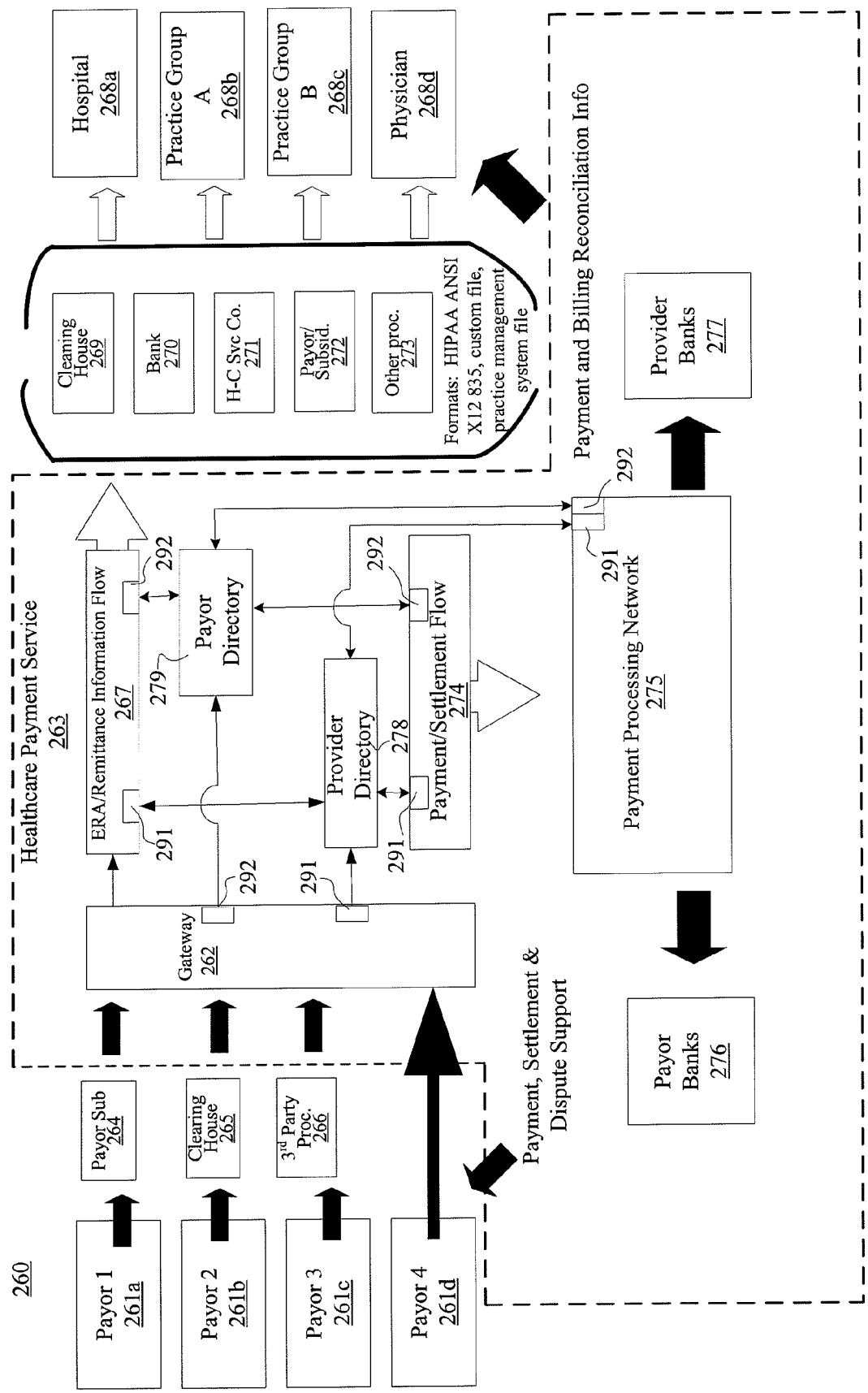
FIG. 2A shows a simplified schematic view of interactions of an alternative embodiment of a payment system in accordance with the teachings of the present invention.

Embodiments in accordance with the present invention are not limited to use with a UBF. FIG. 2A shows a simplified view of an alternative embodiment of a system according to the present invention, which utilizes an electronic healthcare provider directory to facilitate payments between payors and providers.

Specifically, in the system 260 of FIG. 2A, a payor 261a-d may be in electronic communication with gateway 262 of a healthcare payment service 263 either directly, or through an intermediary such as a payor subsidiary 264, clearing house 265, or third party processor 266. As an example, gateway 262 may be configured to receive information including payment/remittance of a healthcare claim according to the American National Standards Institute ANSI X12 standard for electronic data interchange.

Information entering gateway 262 can be routed along different pathways. In one path 267, electronic remittance advice (ERA)/remittance information flows from the healthcare payment service 263 out to providers 268a-d through an intermediary, for example a clearing house 269, a bank 270, a healthcare service company 271, a payor/subsidiary 272, or some other processor 273. Such ERA/remittance information provides details of the particular healthcare claim, for example specific procedures performed, drugs utilized, the identity of the patient, and a breakdown of costs.

In a second path 274, payment and settlement information flows to a payment processing network 275 that is in electronic communication with financial institutions 276 and 277 affiliated with payors 261 and providers 268, respectively. Such payment and settlement information relates to the total value of the healthcare claim that is to be paid, and can include information such as the account numbers of the account from which the funds are to be transferred, and the destination account for the transferred funds. The payment and settlement information may also include a reassociation trace number and payor identification information. The reassociation trace number allows for a unique identification of claims and allows for the uniting of remittance claim information with payment claim information.

Financial institution 276 may be in communication with payors 261 outside of the healthcare payment service regarding payment, settlement, and dispute support. Financial institution 277 may be in communication with providers 268 outside of the healthcare payment service regarding payment and billing reconciliation information.

Healthcare payment service 263 may also include a provider directory 278. Provider directory 278 may be in electronic communication with one or both of the gateway 262 and the payment processing network 275. Provider directory 278 is an electronic database that would function much like the UBF file of the Visa ePay system shown in FIG. 2. Specifically, the provider directory could be referenced to obtain various information relevant to specific providers, for example the providers' bank account information, payment remittance instructions, the contact information at the provider, name and address information, and special instructions.

The information contained in the provider directory could be furnished in advance and then stored on the system. For example, information stored in the provider directory could be furnished by any party authenticated by the provider, including but not limited to the provider itself (such as hospital 268a, Practice Group A 268b, Practice Group B 268c, or Physician 268d), a clearing house, a bank, a healthcare service company, a subsidiary of the payor, or some other third party processor.

During the process flow, all or only a subset of the information stored in the provider directory could then be referenced during the process flow. In the particular embodiment of FIG. 2A, one or more engines 291 may be configured to reference the provider directory based upon recognition of a flag or other specific content of the information (such as provider identity) received at the gateway. In certain embodiments, information stored in the provider directory may not be accessed directly, but may be made available from the directory for reference. Because the information stored by the provider directory is maintained internal to the system, it need not be distributed to the payor or others, and is thus not subject to interception and unauthorized use.

In accordance with embodiments of the present invention, the healthcare payment service could also maintain a Healthcare Payor Directory 279. Healthcare Payor Directory 279 is in electronic communication with one or both of the gateway and the payment processing network. Healthcare Payor Directory 279 could contain specific information relating to the payor. Examples of information held by such a Payor directory 279 could include the payor's bank account information, payment remittance instructions, contact information at the payor, name and address information, and special instructions.

The information contained in the payor directory could be furnished in advance and then stored on the system. For example, information stored in the payor directory could be furnished by any party authenticated by the payor, including but not limited to the payor itself (such as one of payors 261*a-d*), a payor subsidiary, a clearing house, or some other third party processor.

During the process flow, all or only a subset of the information stored in the payor directory could then be referenced during the process flow. In the particular embodiment of FIG. 2A, one or more engines 292 may be configured to reference the payor directory based upon recognition of a flag or other specific content of the information (such as payor identity) received at the gateway. In certain embodiments, information stored in the payor directory may not be accessed directly, but instead may be made available from the directory for reference. Because the information stored by the payor directory is maintained internal to the system, it need not be distributed to the provider or others, and is thus not subject to interception and unauthorized use.

As shown in FIG. 2A, information present in the directories 278 and 279 could be referenced at various points during the transaction flows. For example, the directories could be referenced directly or indirectly to provide information immediately after information enters the gateway. Alternatively, information in the directories could be referenced after the incoming information has left the gateway and been split up into the respective ERA/remittance and payment/settlement flows, respectively. Still further alternatively, information present in the directories could be referenced by the payment processing network.

Utilizing a system including an electronic provider directory and/or payor directory according to certain embodiments, could offer certain advantages. For example, the use of such directories would limit the dissemination of confidential information, such as bank account information, contact information, or special instructions. This could be useful both for reasons of financial security, as well as the privacy concerns that are the subject of HIPAA.

While the healthcare payment service 263 is shown as a single entity in the embodiment of FIG. 2A, this is not required by embodiments of the present invention. According to alternative embodiments, various portions of the healthcare payment service 263 could be administered by different entities.

For example, in one embodiments, the gateway 262 and flows 267 and 274 could be administered by a first entity, for example one that is specifically compliant with HIPAA requirements and qualified to maintain the privacy of healthcare information. By contrast, one or more of the directories 278-279 and the payment processing network receiving the payment and settlement flow could be administered by a second party that is not HIPAA compliant, but which is qualified to maintain the confidentiality of financial transactions.

In one example, an electronic payment service is provided in a healthcare environment, allowing healthcare payers to direct payments to healthcare providers using healthcare-compliant message formats while removing any personal healthcare information. Such a service can allow the providers to avoid the expensive processing of personal checks, while allowing the payer to easily send an electronic payment. The service then can provide the provider with financial reporting regarding the payments, and can handle the user's account information on behalf of the provider.

Figure 3:
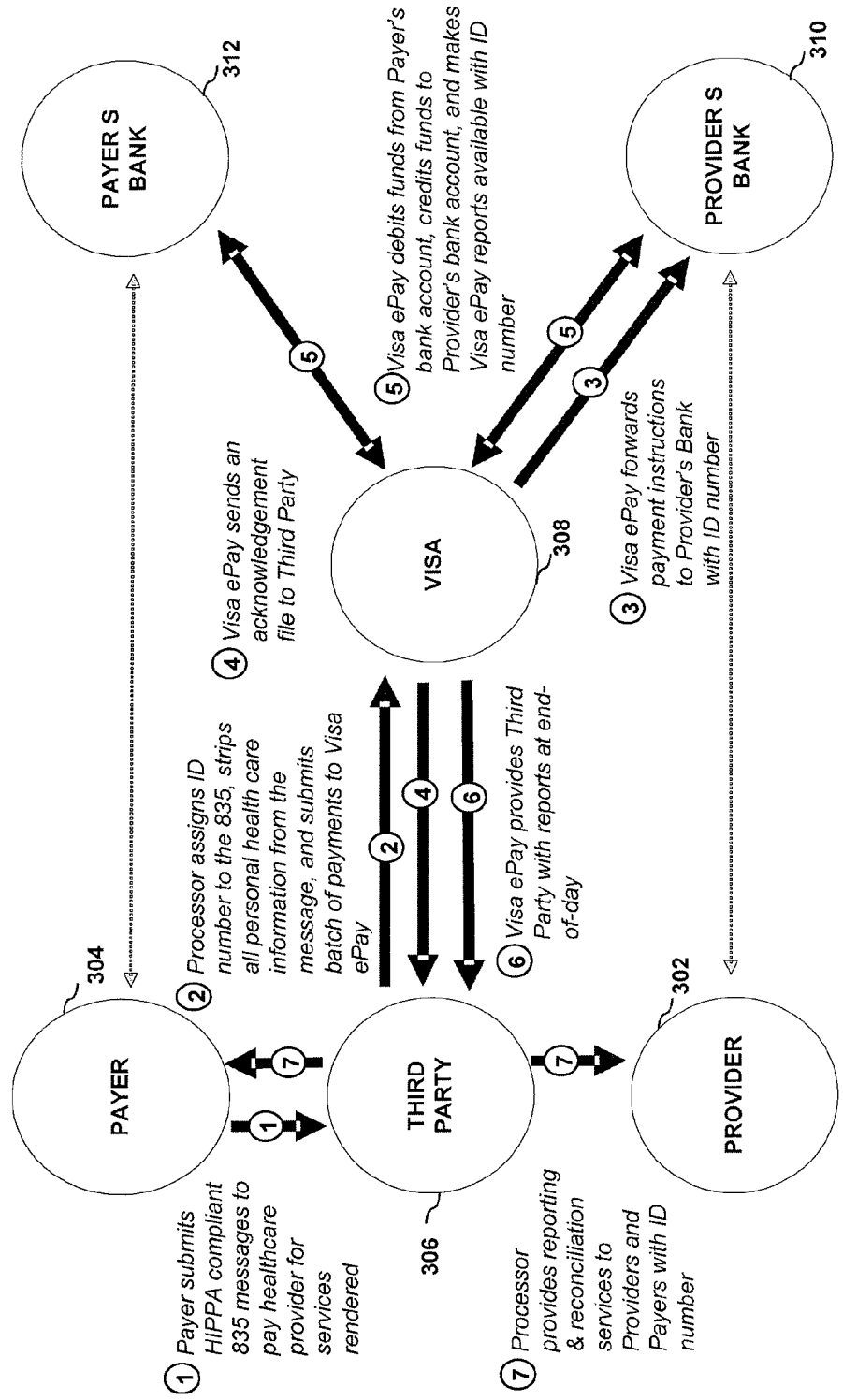
FIG. 3 shows a simplified schematic view illustrating a process flow for payment of healthcare claims utilizing the teachings of the present invention.

FIG. 3 provides a simplified schematic view of an example of a process and settlement flow 300 in accordance with an embodiment of the present invention. Specifically, FIG. 3 shows the interaction between healthcare provider 302 and payer 304, as conducted through third party payment processor 306, electronic payment network administrator 308 (e.g., an entity such as VISA®), a provider bank (or other financial institution) 310 of healthcare provider 302, and a payer's bank (or other financial institution) 312 of payer 304. Each of the foregoing entities may have computational apparatus such as server and/or client computers, and these computational apparatus may be operatively connected together through various communication media.

Prior to initiation of the process and settlement flow 300 shown in FIG. 3, healthcare provider 302 delivers healthcare services and/or goods to the patient. Healthcare provider 302 then forwards to payer 304, a healthcare claim in compliance with §837 of HIPAA. The healthcare provider 302 may forward the healthcare claim through any suitable mechanism including through the Internet or some other suitable computer network. The operation of such computer networks need not described in detail here as they are well known to those of ordinary skill in the art.

Payer 304 receives the healthcare claim, and reviews it for eligibility for payment under existing agreements with the patient (not shown) and with the healthcare provider 302. Based upon the results of this review, a first entity such as the payer 304 submits a first payment message to third party payment processor 306 in compliance with HIPAA §835 to pay healthcare provider 302 for services rendered.

In step 2 of FIG. 3, third party payment processor 306 receives the first payment message in compliance with §835 of HIPAA to pay the healthcare provider 302, and then may perform a number of functions. For example, third party payment processor 306 can assign an ID number (or other identifier) to the §835 message. This ID number can be referenced for designating particular information regarding the particular payment message, and is useful in light of the next step, wherein third party payment processor 306 strips or removes personal healthcare information from the §835 first payment message, and then submits a batch of payments to the payment processing network administrator 308.

The stripping of personal healthcare information can occur in any suitable manner. For example, in one embodiment, a revised message including financial information, but not personal healthcare information can be created using the previously received first message. In another example, personal healthcare information may be deleted from the first message and thereby creating a revised message. In both cases, the stripping of personal information by the third party payment processor 306 essentially renders anonymous the revised payment message that is ultimately sent over the payment processing network. Third party payment processor 306 may also return a notification message to the payer 304, acknowledging receipt of the HIPAA §835 message. This acknowledgment message may include the assigned ID number associated with the revised payment message.

In preferred embodiments, revised payment messages may be aggregated and batched before sending them to various financial institutions. For example, revised payment may be collected throughout the day and may be aggregated and sent in a batch to various financial institutions for processing a predetermined periodic intervals (e.g., once, twice or three times per day).

In step 3 of FIG. 3, payment processing network administrator 308 forwards payment instructions to provider's bank 310 with the ID number. In step 4 of FIG. 3, payment network administrator 308 sends an acknowledgement file to the third party payment processor 306.

In step 5 of FIG. 3, a second entity such as the payment network administrator 308 debits funds from the payer's bank account, credits funds to the provider's bank account, and makes available reports corresponding to the ID number. In step 6 of FIG. 3, the payment network administrator 308 provides the third party payment processor 306 with reports at the end of the day. In step 7 of FIG. 3, the third party payment processor 306 provides reporting and reconciliation services to the provider 302 and the payer 304 with ID numbers.

Any of the reports that are described above may be output to any suitable output device operatively coupled to a computational apparatus (as described above). Suitable output devices include displays, printers, etc. Such reports are useful as they inform various parties including the payer, the provider, the payer's bank, the provider's bank, and the patient with notification that healthcare services have been paid. The reports may include information such as identifiers, payer information, provider information, as well as payment information (e.g., the cost of the service performed as well as the amount paid by the payer).

The embodiment of the electronic payment system illustrated in FIG. 3 offers a number of features that assist in the efficient and accurate processing of healthcare claims. For example, the electronic payment system allows healthcare providers to rapidly and efficiently receive and process Payers' HIPAA §835-compliant payment messages, and creates reports to facilitate the healthcare provider's reconcilement of payer remittances.

The electronic payment system functions to maintain and protect Provider bank account information, handle payment reformatting and routine HIPAA §835 reporting for Provider and Payer reporting, provide Provider's Bank with remittance information, settle with Payer and Provider, provide Provider and Payer with remittance and settlement reporting, and facilitate back-office operations.

Figure 4:
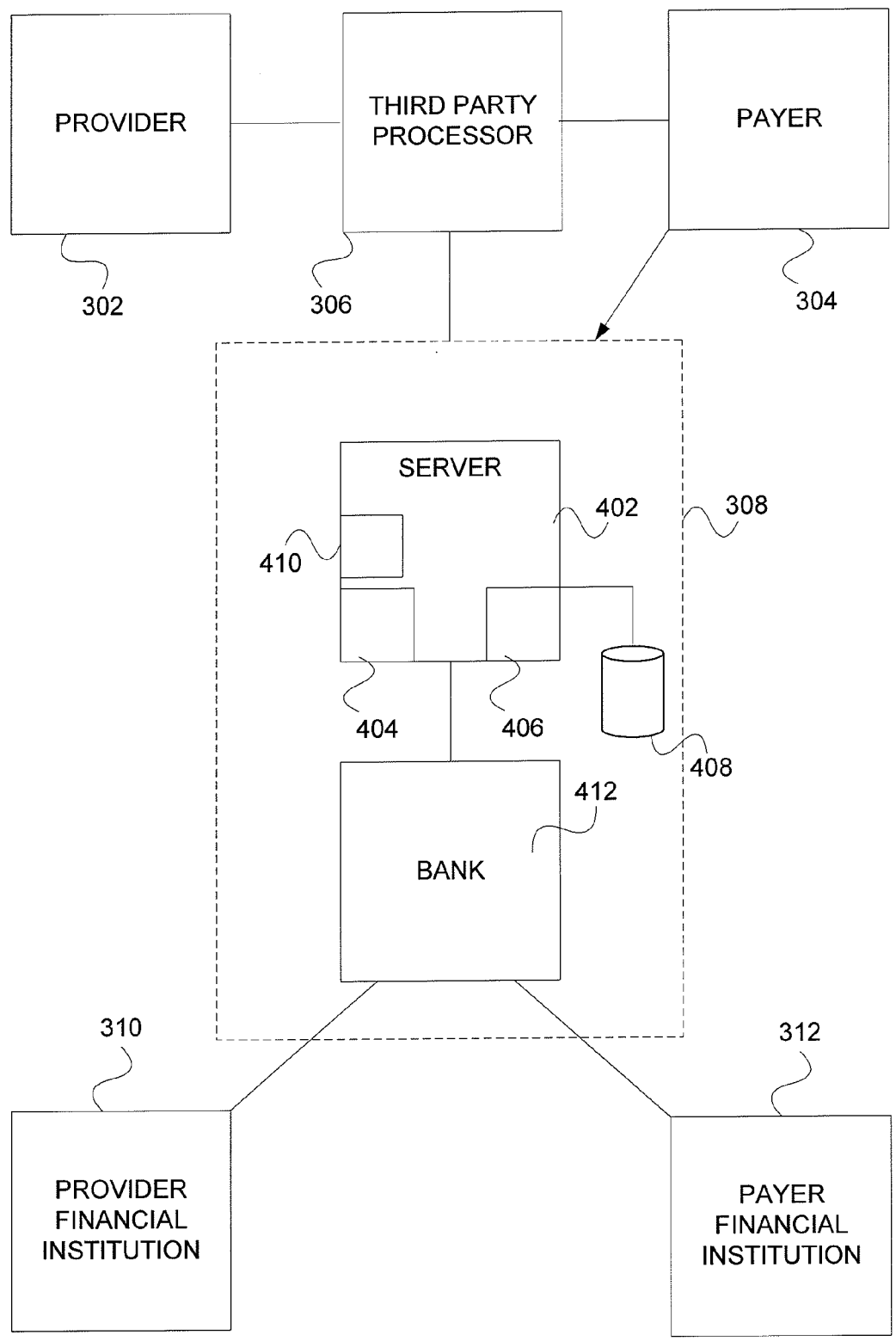
FIG. 4 shows a simplified block diagram of an embodiment of a payment processing system in accordance with the teachings of the present invention.

FIG. 4 shows a simplified block diagram of a system 400 for use in performing payment processing in accordance with an embodiment of the present invention. System 400 comprises payment network administrator 308 in electronic communication with third party processor 306, with financial institution 310 of a healthcare provider 302, and with financial institution 312 of a healthcare payer 304.

The network administered by administrator 308 may include data processing subsystems, networks, and operations used to support and deliver authorization services, exception file services, and clearing and settlement services. An exemplary payment processing network may include VisaNet™. Payment processing networks such as VisaNet™ are able to process credit card transactions, debit card transactions, and other types of commercial transactions. VisaNet™, in particular, includes a VIP system (Visa Integrated Payments system) which processes authorization requests and a Base II system which performs clearing and settlement services.

As shown in FIG. 4, the payment processing network administrator 308 may include a server or host computer 402. A server computer is typically a powerful computer or cluster of computers. For example, the server computer can be a large mainframe, a minicomputer cluster, or a group of servers functioning as a unit. In one example, the server computer may be a database server coupled to a web server. The payment processing network may use any suitable wired or wireless network, including the Internet.

As shown in FIG. 4, the host computer or server 402 of payment network administrator 308 may further include a computer readable storage medium 404 and a processor 406. Server 402 is in electronic communication with a database 408 configured to store information pertaining to financial accounts of payer 304 at financial institution 312 and of healthcare provider 302 at financial institution 310.

An interchange software engine 410 is also shown as part of the payment network administrator 308 in the particular embodiment of FIG. 4. Interchange engine 410 may operate in conjunction with bank 412 of the administrator 308 of the payment processing network, to arrange for the transfer of funds from the financial institution of the payer to the financial institution of the healthcare provider. Interchange engine 410 may also operate to calculate interchange fees and/or perform various other interchange related functions.

Interchange engine 410 and any other software components or functions described in this application, may be implemented as software code to be executed by a processor using any suitable computer language such as, for example, Java, C++ or Perl using, for example, conventional or object-oriented techniques. For example, any of the specific steps (or combination of steps) shown in the Figures of an embodiment of the present application may be embodied as computer code on a computer readable medium in any suitable combination. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

In accordance with certain embodiments of the present invention, the computer-readable storage medium 404 of the host computer 402 may have code stored thereon to direct the processor 406 to perform certain tasks. For example, code stored on the computer readable storage medium may direct the processor to:

receive from a third party payment processor, a payment message in compliance with HIPAA §835 having personal healthcare information stripped therefrom and an ID number added;

forward to payer an acknowledgement of receipt of the payment message, the acknowledgment optionally including the ID number;

perform an interchange function by debiting funds for the healthcare payment from Payer's account at financial institution, and credit funds for the healthcare payment to the healthcare provider's account at financial institution;

provide reports to the third party payment processor identifying payment transactions by ID number, for forwarding on to the payer and healthcare provider for reconciliation purposes.

The particular embodiment of a payment system shown and described in FIG. 4 is provided for purposes of illustration only, and the present invention is not limited to this specific example. Thus, while FIG. 4 shows the payment network administrator as being in electronic communication with a payer and healthcare provider indirectly through a third party processor, this is not required by the present invention.

In accordance with alternative embodiments of the present invention, the third party processor is not present and at least the payer is in direct electronic communication with the administrator of the electronic payment network. In such embodiments, a computer readable storage medium of the administrator of the payment processing network may include code for:

assigning an ID number to the message to allow its tracking in the absence of the personal information stripped from the message.

recognizing personal information present in a HIPAA compliant §837 message;

removing that personal information from the message prior to forwarding the revised message onto the financial institution of the payer; and forward to payer an acknowledgement of receipt of the payment message, the acknowledgement optionally including the ID number;

Examples of personal information of a §835 HIPAA-compliant message which may be removed in accordance with embodiments of the present invention include, but are not limited to the following fields from the NM1 segment of a HIPAA 835 message: last name of patient (NM103), first name of patient (NM104), middle name of patient (NM105), patient prefix (NM106), patient suffix (NM107), patient identifier (NM109), and also the procedure code and procedure line number information identifying the medical procedure.

Examples of types of information of a §835 HIPAA-compliant message which may be retained and forwarded in accordance with embodiments of the present invention include, but are not limited to fields from the following HIPAA §835 segments: BPR (Financial Information); TRN (Trace Information); Loop ID 1000A (Payer Information), including segments N1 (Payer Name), N3 (Payer Address), N4 (Payer Geographic Location), REF (Payer Reference Identification), PER (Payer Contact Information), Loop ID 1000B (Payee Information), including segments N1 (Payee Name), N3 (Payee Address), N4 (Payee Geographic Location), REF (Payee Reference Identification); TSA (Provider Summary Information); CLP (Claim Level Data); CAS (Claims Adjustment); and PLB (Provider Adjustment Data), and provider identifier data, claim identifier data, and the procedure value paid.

Figure 5:
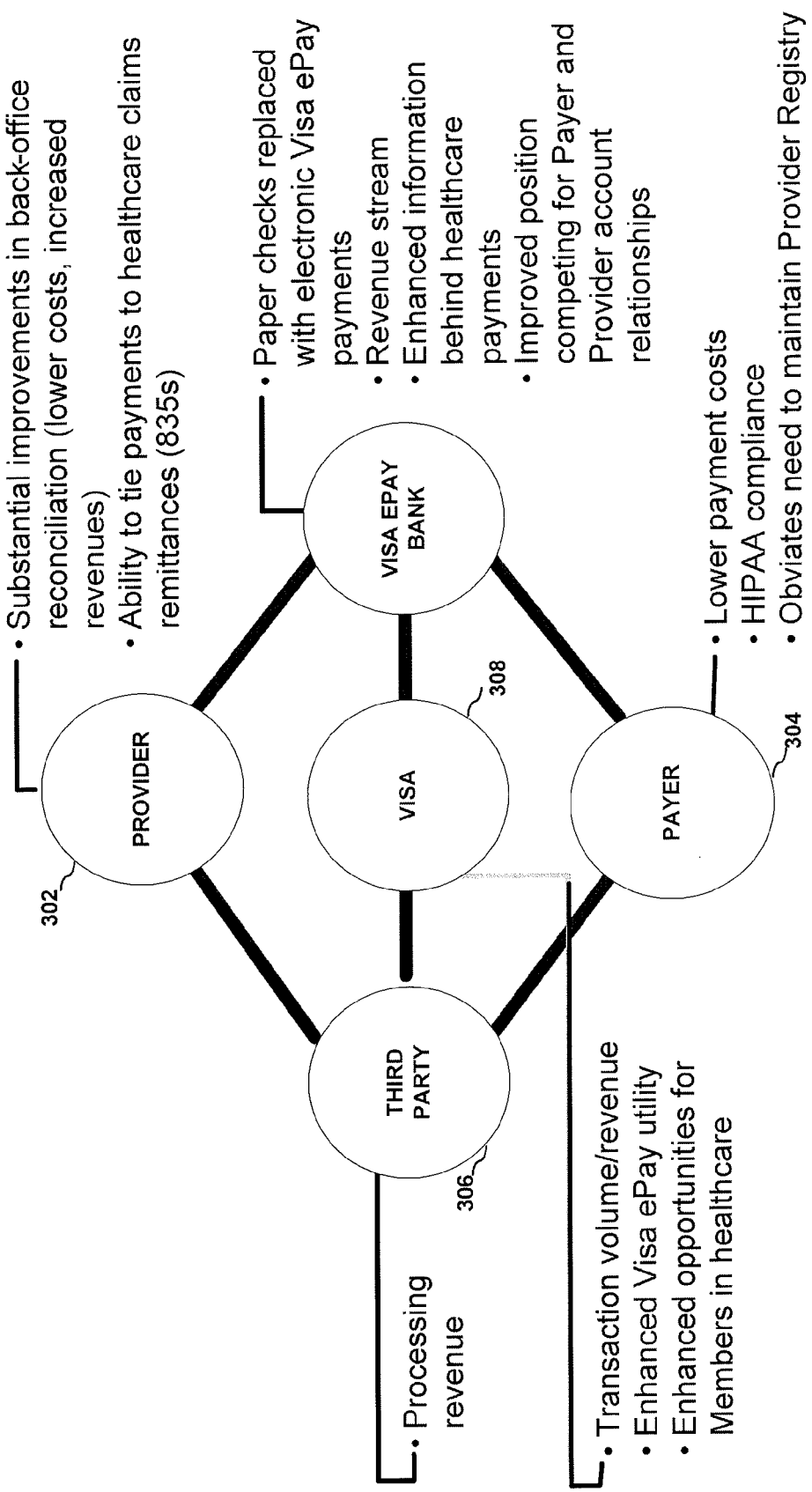
FIG. 5 shows a simplified schematic view illustrating benefits accruing to various elements of the healthcare payment system illustrated in FIG. 3.

As shown in FIG. 5, the embodiment of the electronic payment system illustrated in FIG. 3 offers a number of possible advantages. For healthcare provider 302, the embodiment of the system offers substantial improvement in back-office reconciliation, resulting in lower costs and increased revenues. The system also offers the ability to closely tie payments to healthcare claims remittances (§835s).

For payer 304, embodiments of the system offer lower payment costs, HIPAA compliance, and obviate the need to maintain Provider Registry. For third party processor 306, embodiments of systems in accordance with the present invention offer increased processing revenue.

For administrator 308 of the payment processing network, the embodiment offers an opportunity to increase transaction volume and hence revenue. The healthcare application also offers enhanced utilization of an existing payment functionality (e.g., Visa® ePay). Embodiments of the invention provide enhanced opportunities for members in healthcare.

For the bank 412 of the payment processing network, embodiments in accordance with the present invention offer paper checks replaced with electronic payments, a higher revenue stream, enhanced information behind healthcare payments, and improved position competing for Payer and Provider account relationships.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware, software, and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

While the above embodiment has been described in connection with the ePay electronic payment network administered by an entity such as Visa®, this example is provided for purpose of illustration only, and the present invention should not be limited to this particular electronic payment network. Examples of alternative payment networks which may be utilized in accordance with embodiments of the present invention include, but are not limited to, the Visa® Commerce system and Visa Net™.

Incorporated by reference herein for all purposes are the following U.S. Nonprovisional Patent Applications: Ser. No. 10/418,989, filed Apr. 18, 2003 and entitled "SYSTEM AND METHOD FOR PAYMENT OF MEDICAL CLAIMS"; Ser. No. 11/231,026, filed Sep. 20, 2005 and entitled "METHOD FOR ENCODING MESSAGES BETWEEN TWO DEVICES FOR TRANSMISSION OVER STANDARD ONLINE PAYMENT NETWORKS"; Ser. No. 11/230,761, filed Sep. 20, 2005 and entitled "AUTO SUBSTANTIATION FOR OVER-THE-COUNTER TRANSACTIONS"; and Ser. No. 11/230,743, filed Sep. 20, 2005 and entitled "METHOD AND SYSTEM FOR DETERMINING HEALTHCARE ELIGIBILITY".

Other details of embodiments of the invention can be found in the following U.S. Patent Applications, which are all herein incorporated by reference in their entirety for all purposes: 60/809,857, filed on May 30, 2006; and 60/812,266, filed on Jun. 8, 2006.

Figure 6:
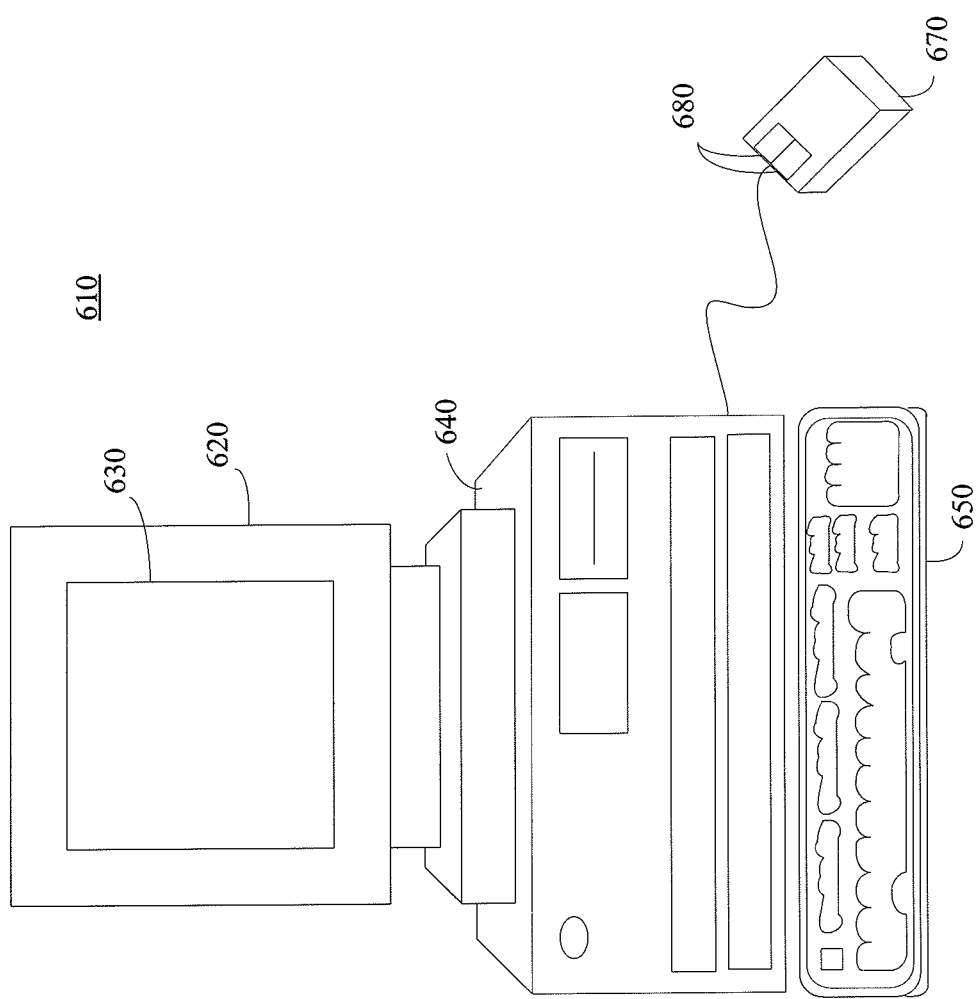
FIG. 6 is a schematic illustration of a computer system for use in accordance with embodiments of the present invention.

A computer system configured to perform various functions of embodiments of the present invention is represented generically in the drawing of FIG. 6. Specifically, FIG. 6 shows computer system 610 including display device 620, display screen 630, cabinet 640, keyboard 650, and mouse 670.

Mouse 670 and keyboard 650 are representative "user input devices." Mouse 670 includes buttons 680 for selection of buttons on a graphical user interface device. Other examples of user input devices are a touch screen, light pen, track ball, data glove, microphone, and so forth. FIG. 6 is representative of but one type of system for embodying the present invention. It will be readily apparent to one of ordinary skill in the art that many system types and configurations are suitable for use in conjunction with the present invention. In one embodiment, computer system 610 includes a Pentium class based computer, running Windows NT operating system by Microsoft Corporation. However, the apparatus is easily adapted to other operating systems and architectures by those of ordinary skill in the art without departing from the scope of the present invention.

As noted, mouse 670 can have one or more buttons such as buttons 680. Cabinet 640 houses familiar computer components such as disk drives, a processor, storage device, etc. Storage devices include, but are not limited to, disk drives, magnetic tape, solid state memory, bubble memory, etc. Cabinet 640 can include additional hardware such as input/output (I/O) interface cards for connecting computer system 610 to external devices external storage, other computers or additional peripherals, further described below.

Figure 6A:
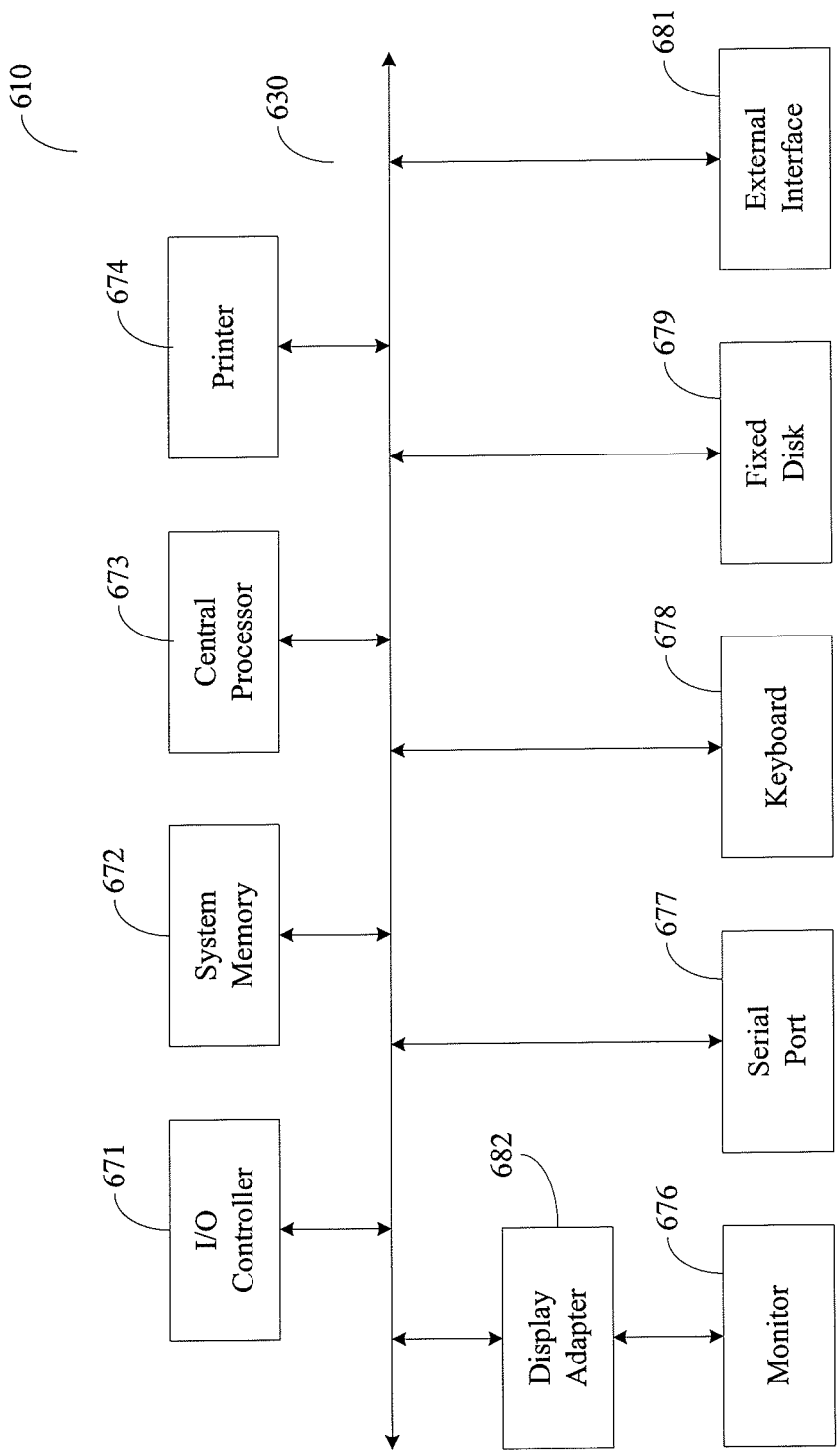
FIG. 6A is an illustration of basic subsystems the computer system of FIG. 6.

FIG. 6A is an illustration of basic subsystems in computer system 610 of FIG. 6. This diagram is merely an illustration and should not limit the scope of the claims herein. One of ordinary skill in the art will recognize other variations, modifications, and alternatives. In certain embodiments, the subsystems are interconnected via a system bus 675. Additional subsystems such as a printer 674, keyboard 678, fixed disk 679, monitor 676, which is coupled to display adapter 682, and others are shown. Peripherals and input/output (I/O) devices, which couple to I/O controller 671, can be connected to the computer system by any number of means known in the art, such as serial port 677. For example, serial port 677 can be used to connect the computer system to a modem 681, which in turn connects to a wide area network such as the Internet, a mouse input device, or a scanner. The interconnection via system bus allows central processor 673 to communicate with each subsystem and to control the execution of instructions from system memory 672 or the fixed disk 679, as well as the exchange of information between subsystems. Other arrangements of subsystems and interconnections are readily achievable by those of ordinary skill in the art. System memory, and the fixed disk are examples of tangible media for storage of computer programs, other types of tangible media include floppy disks, removable hard disks, optical storage media such as CD-ROMS and bar codes, and semiconductor memories such as flash memory, read-only-memories (ROM), and battery backed memory.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A system comprising:
    a processor; and
    a computer readable storage medium, wherein the computer readable storage medium has code stored thereon to direct the processor to implement a method comprising:
    receiving a first electronic payment message from a first entity to a second entity, said first electronic payment message instructing a payment of a healthcare claim on behalf of the first entity, wherein the first electronic payment message is received over a network before the payment is executed or facilitated on an electronic payment processing network that processes credit and debit transactions, and wherein the first entity is a healthcare payor and the second entity comprises a healthcare provider;
    recognizing a type of information in the first electronic payment message, wherein the type of information is associated with a patient and indicative of a healthcare service type;
    generating a revised electronic payment message with an identifier including removing the type of information from the first electronic payment message; and
    forwarding the revised electronic payment message to a third entity to execute or facilitate the execution of the payment using the electronic payment processing network.

2. The system of claim 1 wherein the type of information comprises personal information of a recipient of the payment.

3. The system of claim 1 wherein the first electronic payment message and the revised electronic payment message comprise financial information of a recipient of the payment.

4. The system of claim 1 wherein the first electronic payment message comprises payment instructions for a healthcare claim.

5. The system of claim 1 wherein the revised electronic payment message is in compliance with the Health Insurance Portability and Accountability Act (HIPAA).

6. The system of claim 5 wherein the type of information is selected from:
    a first, last, or middle name of the patient, including prefixes and suffixes; a patient identifier;
    a procedure code; and
    a procedure line number.

7. The system of claim 5 wherein information that is in both the first and revised payment message comprises financial information, trace information, payor information, payee information, provider summary information, claim level data, claims adjustment, or provider adjustment data.

8. The system of claim 5 wherein the system is controlled by a third party healthcare payment processor and the first entity comprises a healthcare payor.

9. The system of claim 5 wherein the system is controlled by an administrator of the electronic payment processing network and the first entity comprises a healthcare payor.

10. The system of claim 1 wherein the code further comprises instructions to cause the system to forward an acknowledgement of receipt of the payment message back to the first entity.

11. The system of claim 10 wherein the identifier includes an identification number and wherein the acknowledgment includes the identification number.

12. A method of processing a healthcare payment, the method comprising: receiving from a healthcare payor, at a server computer, a first electronic message instructing payment of a healthcare claim on behalf of the healthcare payor to a healthcare provider, wherein the first electronic message is received before a payment is executed or facilitated on an electronic payment processing network that processes credit and debit transactions;

recognizing in the first electronic message a type of information at the server computer, wherein the type of information is associated with a patient and indicative of a healthcare service type;

generating a revised electronic payment message with an identifier including removing the type of information from the first electronic payment message at the server computer; and forwarding the revised electronic payment message from the server computer to a second entity to generate or facilitate execution of a payment using the electronic payment processing network.

13. The method of claim 12 wherein the first electronic message is in compliance with the Health Insurance Portability and Accountability Act (HIPAA).

14. The method of claim 13 wherein the type of information comprises:

a first, last, or middle name of the patient, including prefixes and suffixes; a patient identifier;

an identity of a medical procedure performed; and a description of the medical procedure performed.

15. The method of claim 13 wherein information that is in both the first electronic message and the revised electronic payment message comprises financial information, trace information, payer information, payee information, provider summary information, claim level data, claims adjustment, or provider adjustment data.

16. The method of claim 12 wherein a third party processor of healthcare claims generates the revised electronic payment message.

17. The method of claim 12 wherein an administrator of the electronic payment network generates the revised electronic payment message.

18. The method of claim 12 further comprising forwarding an acknowledgement of receipt of the electronic payment message back from the server computer to the healthcare payor.

19. The method of claim 18 wherein the acknowledgment includes the identifier, and wherein the identifier comprises an identification number.

20. The method of claim 12 further comprising generating a report including the identifier associated with the revised payment message.

21. The system of claim 1, wherein the first entity does not have access to the second entity.

22. The system of claim 1, wherein the revised electronic payment message and other revised electronic payment messages are aggregated and batched before they are forwarded to the third entity.

\* \* \* \* \*